United States Patent
Heilig et al.

(10) Patent No.: US 10,950,345 B2
(45) Date of Patent: Mar. 16, 2021

(54) METHODS, APPARATUS, AND SYSTEMS FOR INTEGRATION OF DIAGNOSTIC LABORATORY DEVICES

(71) Applicant: Siemens Healthcare Diagnostics Inc., Tarrytown, NY (US)

(72) Inventors: Brian Heilig, West Berlin, NJ (US); Jeffrey Hoffman, Lebanon, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 16/968,343

(22) PCT Filed: Mar. 7, 2019

(86) PCT No.: PCT/US2019/021077
§ 371 (c)(1),
(2) Date: Aug. 7, 2020

(87) PCT Pub. No.: WO2019/182756
PCT Pub. Date: Sep. 26, 2019

(65) Prior Publication Data
US 2020/0395121 A1 Dec. 17, 2020

Related U.S. Application Data

(60) Provisional application No. 62/647,235, filed on Mar. 23, 2018.

(51) Int. Cl.
*G16H 40/00* (2018.01)
*G16H 40/63* (2018.01)
(Continued)

(52) U.S. Cl.
CPC ............ *G16H 40/63* (2018.01); *G06F 16/22* (2019.01); *G16H 10/40* (2018.01); *H04L 67/12* (2013.01)

(58) Field of Classification Search
None
See application file for complete search history.

(56) References Cited

U.S. PATENT DOCUMENTS 5,243,992 A * 9/1993 Eckerle ............... G04G 21/025
600/485
8,364,500 B2 * 1/2013 Eisenberger ........... G06Q 10/00
705/2

(Continued)

OTHER PUBLICATIONS

International Search Report for PCT/US2019/021077 dated May 13, 2019.

(Continued)

*Primary Examiner* — Farhan M Syed

(57) ABSTRACT

Methods, apparatus, and systems for obtaining sensor-generated data in a diagnostic laboratory apparatus including one or more producers of data that include a sensor, a local communications network communicatively coupling the producers to a data router configured to translate data received from producers of data into a common format record, the common format including key-value pairs, and at least one subscriber that registers one or more channel-based subscriptions with the data router. Records remain in storage by the data router until to the subscriber acknowledges successful receipt, after which the data router manages its storage resources to provide storage for newer sensor-generated data. The data router is configured to install plug-ins as needed to translate data formats of newly-integrated producers with new formats.

20 Claims, 10 Drawing Sheets

(51) Int. Cl.
*G16H 10/40* (2018.01)
*G06F 16/22* (2019.01)
*H04L 29/08* (2006.01)

(56) References Cited

U.S. PATENT DOCUMENTS

| | | | | | |
|---|---|---|---|---|---|
| 8,566,157 | B1* | 10/2013 | Zhang | ................ | G06Q 30/0277 |
| | | | | | 705/14.45 |
| 8,948,465 | B2* | 2/2015 | Tiwari | ................ | G06K 9/6218 |
| | | | | | 382/115 |
| 9,195,893 | B2* | 11/2015 | Tiwari | ................ | G06F 16/5838 |
| 9,275,093 | B2* | 3/2016 | Pandey | ................... | H04L 67/12 |
| 9,292,749 | B2* | 3/2016 | Tiwari | ................ | G06F 16/532 |
| 10,169,434 | B1* | 1/2019 | Block | ................... | G06F 16/254 |
| 10,534,791 | B1* | 1/2020 | Block | ................... | G06F 16/248 |
| 2012/0197898 | A1* | 8/2012 | Pandey | ............... | G06F 16/2264 |
| | | | | | 707/741 |
| 2013/0266193 | A1* | 10/2013 | Tiwari | ................ | G06F 16/5854 |
| | | | | | 382/115 |
| 2015/0178569 | A1* | 6/2015 | Tiwari | ................ | G06K 9/6807 |
| | | | | | 382/115 |
| 2016/0034765 | A1* | 2/2016 | Tiwari | ................ | G06K 9/6218 |
| | | | | | 382/115 |
| 2016/0148109 | A1* | 5/2016 | Watanabe | .......... | G06K 9/00335 |
| | | | | | 706/48 |
| 2017/0075778 | A1* | 3/2017 | Heliker | ............ | G06Q 10/06312 |
| 2018/0131516 | A1* | 5/2018 | Meng | .................... | H04L 9/0643 |
| 2019/0095478 | A1* | 3/2019 | Tankersley | .......... | G06F 16/2379 |
| 2020/0285997 | A1* | 9/2020 | Bhattacharyya | ....... | G06N 20/00 |

OTHER PUBLICATIONS

Redox Engine description, retrieved from internet Mar. 2018, https://developer.redoxengine.com/introduction/how-redox-works/.

* cited by examiner

| Subscriber ID | Channel ID | Topic ID | Last Record Sent ID | Last Record Rec'vd ID |
|---|---|---|---|---|
| 902 | 904 | 906 | 908 | 910 |

METHODS, APPARATUS, AND SYSTEMS FOR INTEGRATION OF DIAGNOSTIC LABORATORY DEVICES

FIELD

This disclosure relates to methods, apparatus, and systems for integration of diagnostic laboratory devices.

BACKGROUND

Automated diagnostic analysis apparatus (e.g., chemical analyzers or immunoassay instruments) may be used to analyze patient specimens. Patient samples or specimens may include, e.g., urine, blood serum or plasma, saliva, cerebrospinal liquids, various tissue samples, and the like. Automated diagnostic analysis apparatus are used to improve operating speed and efficiency as compared to (1) manual operation of analyzers or instruments; (2) manual transport and positioning of specimen containers; and (3) manual recordation and transmission of test, measurement, and analysis information.

Automated diagnostic analysis apparatus in a diagnostic laboratory setting are frequently configured to operate with multiple pieces of equipment, and a track system for the transport of samples or specimens. A process manager may be incorporated in such a system to direct the operation of the various analyzers, transport tracks, centrifuges, environmental sensors, and the like. Such process managers receive information about the various apparatus and operations, and in some instances, may generate control information based thereon.

SUMMARY

According to a first embodiment, a method of operating a diagnostic laboratory system to provide sensor-generated information is provided. The method includes providing a producer, a data router, and a subscriber, obtaining, by the producer, sensor-generated data, and receiving, by the data router, information, including sensor-generated data, from the producer. The method further includes generating, by the data router, a record based on at least the sensor-generated data from the producer, wherein the record has one or more key-value pairs, associating, the record with an associated channel identifier, storing the record to provide a stored record such that the stored record is retrievable based, at least in part, on the associated channel identifier, and maintaining an index having an index value, the index associated with a subscription of the subscriber. And the method further includes retrieving the stored record, responsive to determining that a channel identifier requested by the subscriber matches the associated channel identifier to provide a retrieved record, transmitting information based, at least in part, on the retrieved record and the index value, to the subscriber, storing the value of the index in a table to indicate the index value of the retrieved record sent to the subscriber, updating the index to provide a updated index value, and deleting the stored record, responsive, at least in part, to receiving an acknowledgement from the subscriber that the information based, at least in part, on the retrieved record and the index value, was successfully received by the subscriber. In this example embodiment the producer includes at least one sensor, and a first computational resource, the first computational resource comprising a processor, at least one communications network interface, and a memory having stored therein a plurality of instructions, the data router includes at least one communications network interface, and a second computational resource comprising a processor, and a memory having stored therein a plurality of instructions and a plurality of tables, and the subscriber includes a third computational resource comprising a processor, at least one communications network interface, and a memory having stored therein a plurality of instructions, and the data from the producer is obtained, at least in part, from operation of at least one sensor coupled to the producer, the at least one sensor disposed external to the data router.

According to another embodiment, a data router is provided. The data router includes at least one communications network interface, and a computational resource that includes a processor, and a memory having stored therein at least one table, at least one index, and a plurality of instructions that, when executed by the processor, cause the data router to receive information, including sensor-generated data in a first format, from a producer; translate the information to generate a record based on at least the sensor-generated data in the first format, wherein the record is in a second format and has one or more key-value pairs; associate the record with an associated channel identifier; store the record to provide a stored record such that the stored record is retrievable based, at least in part, on the associated channel identifier; maintain an index having an index value, the index associated with a subscription of a subscriber; retrieve the stored record, responsive to determining that a requested channel identifier of the subscription of the subscriber matches the associated channel identifier, to provide a retrieved record; transmit to the subscriber, information based, at least in part, on the retrieved record and the index value; store the value of the index in a first table of the at least one table, to indicate the index value of the retrieved record sent to the subscriber; update the index to provide an updated index value; and delete the stored record, responsive, at least in part, to receiving an acknowledgement from the subscriber that the information based, at least in part, on the retrieved record and the index value, was successfully received by the subscriber.

According to another embodiment, a diagnostic laboratory apparatus is provided. The diagnostic laboratory apparatus includes a producer, a subscriber, and a data router communicatively coupled to the producer, and communicatively coupled to the producer. The data router includes at least one communications network interface, and a first computational resource. The first computational resource includes a processor, and a memory having stored therein a plurality tables, and having a plurality of instructions stored therein that, when executed by the processor, cause the data router to receive information, including sensor-generated data in a first format, from the producer, generate a record based on at least the sensor-generated data in the first format from the producer, wherein the record is in a second format and has one or more key-value pairs, associate the record with an associated channel identifier, store the record to provide a stored record such that the stored record is retrievable based, at least in part, on the associated channel identifier, maintain an index having an index value, the index associated with a subscription of the subscriber, retrieve the stored record, responsive to determining that a requested channel identifier of the subscription of the subscriber matches the associated channel identifier, to provide a retrieved record, transmit to the subscriber, information based, at least in part, on the retrieved record and the index value, store the value of the index in a first table of the plurality of tables, to indicate the index value of the retrieved record sent to the subscriber, update the index to provide an updated index value, and delete the stored record, responsive, at least in part, to receiving an acknowledgement from the subscriber that the information based, at least in part, on the retrieved record and the index value, was successfully received by the subscriber. In this example embodiment, the producer includes at least one sensor, and a second computational resource. The second computational resource includes a processor, at least one communications network interface, and a memory having stored therein a plurality of instructions that, when executed by the processor, cause the producer to operate the at least one sensor, and obtain sensor-generated data. In this example embodiment, the subscriber includes a third computational resource that includes a processor, at least one communications network interface, and a memory having stored therein a plurality of instructions that, when executed by the processor, cause the subscriber to register with the data router and receive information based, at least in part, on the retrieved record and the index value.

Still other aspects, features, and advantages of this disclosure may be readily apparent from the following detailed description illustrated by a number of example embodiments and implementations, including the best mode contemplated. This disclosure may also be capable of other and different embodiments, and its several details may be modified in various respects. Thus, the disclosure is to be regarded as illustrative in nature, and not as restrictive. This disclosure covers all modifications, equivalents, and alternatives falling within the scope of the claims.

BRIEF DESCRIPTION OF THE DRAWINGS

The drawings are to be regarded as illustrative in nature, and not as restrictive. The drawings are not necessarily drawn to scale.

FIG. 9 illustrates an example data table storing in accordance with various example embodiments.

DETAILED DESCRIPTION

Overview

Figure 1:
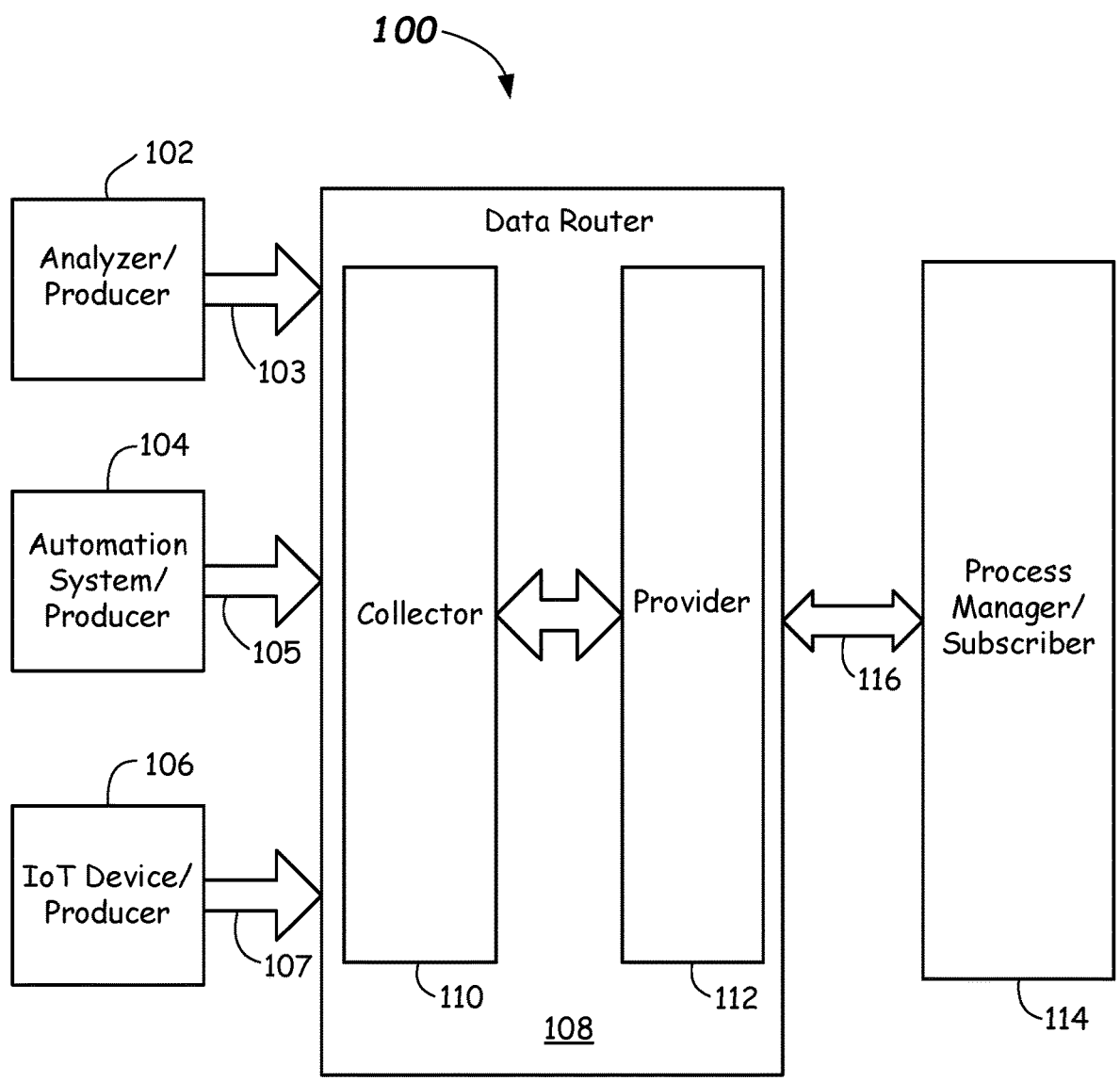
FIG. 1 illustrates a block diagram of producers and a subscriber coupled by a data router and showing data flow in accordance with various example embodiments.

Digitalization, Artificial Intelligence (AI) and the Internet of Things (IoT) are emerging technologies that are rapidly affecting a number of industries, including healthcare. These emerging technologies deal with, among other things, the acquisition and analysis of data. Systems that facilitate data gathering, and offer augmentation of that data for seamless action and insights are believed to be of particular value in the marketplace in general, and in healthcare laboratory automation systems in particular.

One of the purposes of a medical diagnostic laboratory is to perform tests on clinical samples or specimens to obtain information about the health of a patient. In a medical diagnostic laboratory there exist many devices that communicate with each other using various protocols. Such communication may be conducted over a transmission control protocol (TCP) connection. Data exchanged between these devices may be classified into three non-exclusive categories: clinical data, service data, and operational data. Clinical data relates to information about the analysis of a sample or specimen, and represents the primary function of a medical diagnostic laboratory. Service data aids in the servicing of a device by a technician, either remotely or on-site.

Operational data relates to information, such as inventory or alert information, used for management of the medical diagnostic laboratory.

For historical reasons the diagnostic laboratory architecture tends to be a closed system wherein laboratory devices are tightly coupled with one another. This tight coupling results in the integration of new capability, or new laboratory devices being a slow and difficult process. The protocols implemented by laboratory devices in conventional diagnostic laboratory systems are commonly found to have been designed for point-to-point systems. Thus, access to the information exchanged between these laboratory devices requires modifications to their software to expose the data to new systems. These protocols also tend to be outdated, obscure, and require significant domain knowledge to interpret.

In various embodiments, the data router provides a streaming and/or a query data access capability. In the streaming model data is pushed from producers to the data router where it is translated into a predetermined format and stored pending retrieval for delivery to subscribers. In the query model data is queried by the subscriber using a predetermined protocol. That query is translated and forwarded to the associated producer which provides the requested data, which is again translated by the data router and forwarded back to the requesting subscriber.

In accordance with this disclosure, various embodiments are directed to a diagnostic laboratory system and the operation thereof. Such operations may include, but are not limited to, producing, by laboratory device, clinical, service and/or operational data, communicating that data to a data router, translating that data into a uniform format, and publishing the uniform format data to subscribers that have registered subscriptions with the data router.

Some embodiments may be further directed to integration of heterogeneous laboratory devices into a diagnostic laboratory system such that sensor-generated data produced by the laboratory devices, which are in a respective heterogeneous plurality of data formats, can be presented in a uniform format to one or more subscribers to, or consumers of, such data in the diagnostic laboratory system.

Various embodiments, in accordance with this disclosure, provide a data router coupled between one or more producers, and one or more subscribers, such that the data router receives sensor-generated data from a producer, translates that data into a format that is readable by the subscribers in the system, and stores the translated data until it can be transmitted to a designated subscriber. After it is determined that the transmission to the designated subscriber has been successfully completed, the data router may delete such stored information to free up space in the memory, or storage subsystem, of the data router. To accommodate producer-specific data formats of a variety of producers present in a system, the data router may be configured to translate received sensor-generated data from each producer into records having a common format that is readable by the one or more subscribers in the system. In various embodiments, the translation operation produces records having one or more key-value pairs.

In some example embodiments, the data router is a combination of hardware and software that acts as a publisher between data sources (i.e., producers) and data consumers (i.e., subscribers). In various alternative embodiments, the data router may be implemented as hardware, e.g., logic circuits, without software intended to be executed by a processor. Producers register a "channel" with the data router.

In various embodiments, the channel is a logical construct that allows a producer to label information that conforms to certain constraints and conditions such that the labelled information can be recognized by the data router as originating from a specific producer's registered channel. In some example embodiments, registering a channel by the producer with the data router includes communication between the producer and the data router, together with action by both the producer and the data router. The communication between the producer and the data router may be conducted through any suitable means, wired or wireless. The action taken by the producer is to maintain a channel identification label that accompanies its data so that the data router can properly store the data and later provide the data associated with that channel to a subscriber that requests data from that channel.

After registering a channel with the data router, a producer may send data in a predetermined format, to the data router. In some example embodiments, the data router is format/protocol agnostic, meaning that the data router may accept the data sent by the producer in any predetermined format. In various embodiments in accordance with this disclosure, the data router may translate the data received from the producer into records in a different format, for example, but not limited to, key-value pairs. In some example embodiments data is sent from the producer to the data router via a communications network, such as but not limited to a local area network (LAN). The producers and the data router may be physically co-located, or may be physically remote from each other. The communications network between the producer and the data router may be wired, wireless, or a combination of wired and wireless. By "co-located," it is meant that the data router and the producers are located within the same room, or within the same building.

Subscribers are consumers of the information generated by the producers. In example embodiments that have a plurality of producers, a subscriber may be interested in receiving information from one or more specific combinations of producers. The subscribers register, with the data router, those channels in which they are interested. That is, a subscriber communicates with the data router to identify the channels from which it wants to receive published data or information. The subscriber then receives the requested published data or information from the corresponding producer(s), after translation by the data router, as it becomes available. In some example embodiments, the data router can store the translated data until all of the subscribers to a particular channel have received the translated data. The data router may manage its memory and/or data storage resources such that records containing the translated data are deleted from the memory or data storage resources after such records have been successfully received by the registered subscribers.

Terminology

As used herein, the term "producer" refers to a laboratory device that is configured to, among other things, operate one or more sensors, obtain sensor generated data, and/or provide the sensor generated data to a data router. Producers may be, but are not limited to, laboratory diagnostic analyzers, centrifuges, automation systems, informatics products, and IoT devices.

As used herein, "data router" refers to a computational resource, e.g., a computer system, that is configured to, among other things, receive data from one or more producers, and organize the received data for transmission in one or more channels. Such data routers are further configured to store, at least temporarily, some or all of the data received from the producers. In some embodiments, that data may be the producer-originated data translated into a uniform format prior to being stored. In alternative embodiments, that data may be stored first, and translated later.

As used herein, "subscriber" refers to a computational resource that is configured to present a request to a data router for information from one or more producers, or more specifically from one or more channels. A subscriber may be further configured to receive the requested information from the one or more channels via the data router which transmits data associated with the requested one or more channels to the subscriber. A subscriber can be any system or subsystem that uses data, and may be, but is not limited to, a computer system, a management program, an informatics product, or a third party application (e.g., software executed by a computational resource), etc.

As used herein, "computational resource" refers to a device configured to carry out one or more predetermined data processing and/or data communication tasks. Such computational resources can be implemented entirely by hardware, e.g., digital and/or analog circuits, or by a combination of a processor and a memory coupled thereto having instructions stored therein that, when executed by the processor, cause the computational resource to perform the one or more predetermined data processing and/or data communication tasks.

The term "IoT" is an acronym for Internet of Things.

As used herein, "IoT device" refers to a device that is configured to make one or more measurements of its environmental or ambient conditions, generate data based on the one or more measurements, and transmit that data by wired or wireless communication, or a combination of wired and wireless communication. IoT devices may include sensors such as, but not limited to, temperature sensors, infrared sensors, visible light sensors, ultraviolet sensors, X-ray sensors, pressure sensors, acceleration sensors, voltage sensors, current sensors, magnetic sensors, barometric sensors, humidity sensors, and water ionization sensors.

The term "WebSocket" refers to computer communications protocol providing full-duplex communication channels over of single TCP connection. The WebSocket protocol is standardized by the Internet Engineering Task Force (IETF) as RFC 6455. The WebSocket Protocol enables two-way communication between a client running untrusted code in a controlled environment to a remote host that has opted-in to communications from that code. The security model used for this is the origin-based security model commonly used by web browsers. The protocol includes of an opening handshake followed by basic message framing, layered over TCP. The goal of WebSocket is to provide a mechanism for browser-based applications that need two-way communication with servers that does not rely on opening multiple hypertext transport protocol (HTTP) connections. In the context of various embodiments in accordance with this disclosure, WebSocket may be used to provide access to real-time data. With WebSocket data may be sent immediately to a subscriber with a websocket connection when that data arrives at the data router.

The expression "key-value pair" refers to a data structure having two linked data items; a key, which is an identifier for an associated value, and the value. An example of a key-value pair data structure is shown in Table 1, below.

TABLE 1 key-value pair data structure example

| KEY | VALUE |
|---|---|
| Producer Type | Clinical Chemistry Analyzer |
| First Name | John |
| Last Name | Doe |

FIG. 1 illustrates an example diagnostic laboratory network 100, in accordance with some embodiments of this disclosure, having producers 102, 104, and 106. In this example embodiment, producer 102 is an analyzer such as, but not limited to, a blood analyzer, immuno-assay analyzer, and clinical chemistry analyzer. Producer 104, in the example embodiment, is an automation system that provides a track system for moving samples between analyzers. In addition to the track itself, there may be other automation-specific modules present on the track such as one or more centrifuges, one or more refrigerated storage units, one or more bulk input modules, one or more decappers, and the like. Producer 106, in the example embodiment, is an IoT device, such as but not limited to one or more temperature sensors, pressure sensors, infrared sensors, light sensors, ultraviolet sensors, X-ray sensors, acceleration sensors, barometers, humidity sensors, and water ionization sensors. Producers 102, 104, and 106, communicate information 103, 105, 107 they respectively obtain in the course of their operations. Information 103, 105, and 107 may be in a producer-specific format. That is, each producer 102, 104, and 106 may present information in its own specific format.

In this example embodiment, data router 108 may be a computer system, and information 103, 105, 107 may be communicated between producers 102, 104, 106 respectively and data router 108 via any suitable communications network, wired or wireless. In some example embodiments, to improve data security, the Internet is avoided, and communication between producers and data router is performed within a locally controlled network environment.

Still referring to FIG. 1, data router 108 may include a collector module 110 and a provider module 112. Collector module 110 is responsible for managing the low-level network communication protocols between producers 102, 104, and 106, and data router 108, and is further responsible for translating the producer-specific formats into a common format including key-value pairs. Provider module 112 is responsible for interacting with one or more subscribers 114. Provider module 112 establishes a subscription for each subscriber 114, and is further responsible for providing data to the subscribers 114 as it becomes available after translation by collector 110. Provider 112 communicates with subscriber 114 via a network communications path 116. Collector module 110 and provider module 112 may be implemented as a computer system executing one or more programs, i.e., sets of instructions.

As described above, subscribers, such as subscriber 114, may make a request to receive data or information, originally generated by a producer, from data router 108 via a requested channel. In various example embodiments, data router 108 translates the various producer-specific formats in which it receives data, into a common format including key-value pairs that can be understood by all of its subscribers 114.

Figure 2:
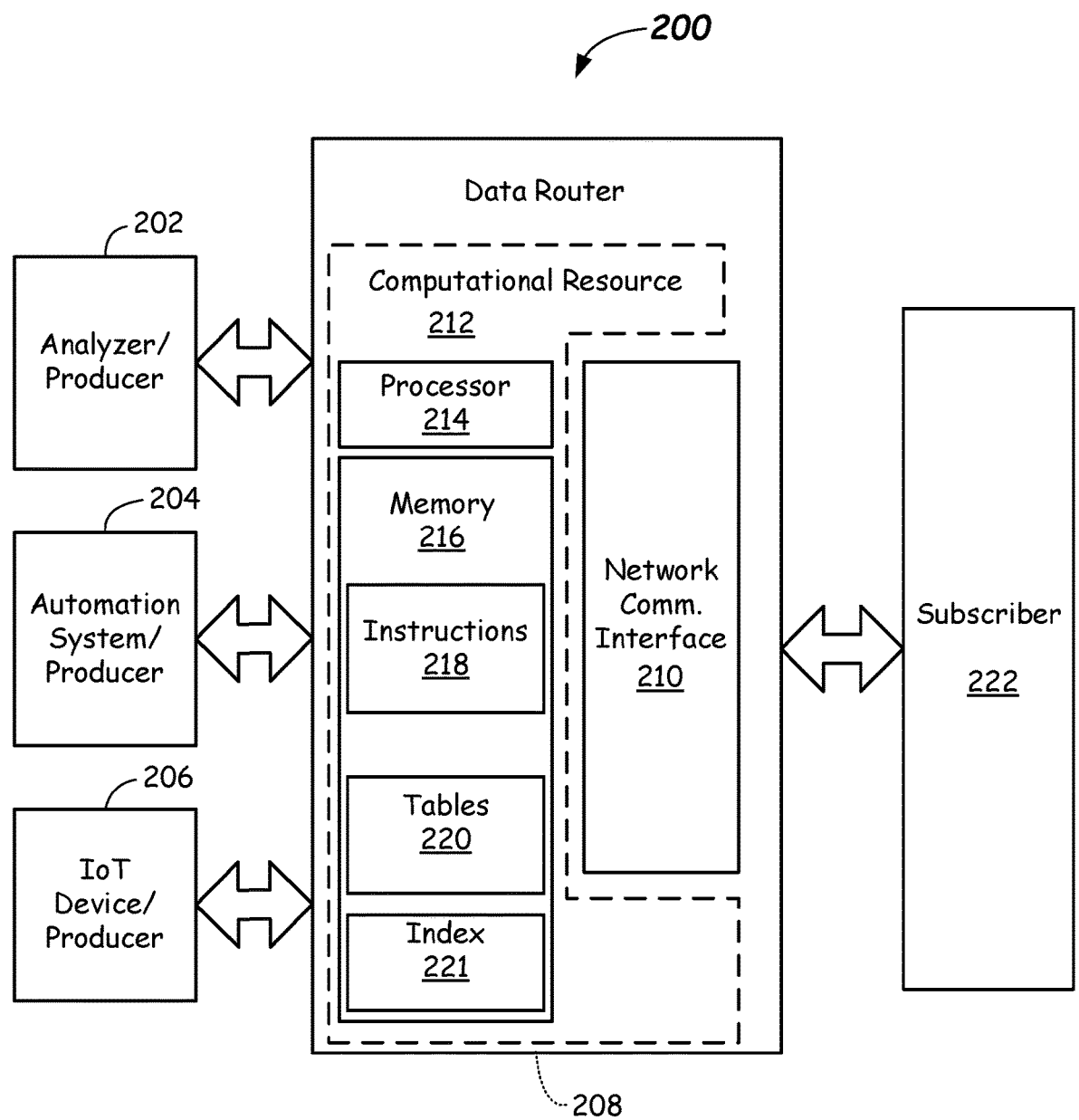
FIG. 2 illustrates a block diagram of producers and a subscriber coupled by a data router, and various internal blocks of a data router in accordance with various example embodiments.

FIG. 2 illustrates an example diagnostic laboratory network 200, in accordance with some embodiments of this disclosure, having producers 202, 204, and 206. In this example embodiment, producers 202, 204, and 206 are each configured to measure various parameters, generate, and/or obtain data or information and produce, via hardware or hardware/software combinations, first packets of data or information in a native format, i.e., a producer-specific format. The aforementioned hardware/software combinations refer to computer systems such as the computer system discussed below in connection with FIG. 6. Such computer systems accomplish their tasks by executing instructions stored in their respective memories. By executing such instructions the first packets of data or information are logically constructed, formatted, and communicated. In this example embodiment, producer 202 is an analyzer such as, but not limited to, a blood analyzer. Producer 204 is an automation system that provides a track system for moving containers of samples or specimens between analyzers. As an automation system, producer 204 may obtain data related to a status of the automation system functions to produce a first automation system report for eventual communication to a subscriber. Producer 206 is an IoT device, including but not limited to, one or more temperature sensors, pressure sensors, voltage sensors, current sensors, infrared sensors, light sensors, ultraviolet sensors, X-ray sensors, barometers, humidity sensors, and water ionization sensors. As an IoT device, producer 206 may obtain data related to a sensor of the IoT device to produce an IoT report. Producers 202, 204, and 206, communicate information that they respectively obtain in the course of their operations.

FIG. 2 further shows that information is communicated to a data router 208. In this example embodiment, data router 208 may include a network communications interface 210, and a computational resource 212. The information may be communicated between producers 202, 204, 206 respectively and data router 208 via any suitable communications network, wired or wireless, and the network communications interface 210 of data router 208. In some example embodiments the communications network is an Ethernet local area network, and network communications interface 210 is an Ethernet local area network interface. In some example embodiments, this communication takes place over a local network, and without accessing the Internet.

As illustrated in FIG. 2, computational resource 212 may include a processor 214, a memory 216, instructions 218 stored in memory 216, and data structures such as tables 220 and index 221 stored within memory 216.

Still referring to FIG. 2, a subscriber 222 is shown wherein subscriber 222 is a process manager. Subscriber 222 may be implemented as a computer system executing one or more programs. As described above, a subscriber 222 may make a request to receive data or information, originally generated by a producer, via a requested channel from data router 208. In such an arrangement, subscriber 222 receives data or information in a common format that includes one or more records having key-value pairs. By "common format," it is meant that the various producer-specific formats are translated by data router 208 such that any subscriber may work with those records without being aware of the format in which the originating producer provided the data. This technological solution provides diagnostic laboratory systems in accordance with this disclosure with an improved ability to integrate additional producers into a system without having to make changes to the subscriber. In some example embodiments, a plug-in can be added to data router 208 each time a new producer is integrated into diagnostic laboratory network 200 where that new producer provides data in a unique format, i.e., a format that data router 208 does not have the ability to translate. Because data router 208 is configured to incorporate plug-ins specific to each new translation operation, diagnostic laboratory network 200 can be easily modified by integrating new producers, e.g., lab devices, into the system. Plug-ins are a software component that adds a specific feature to an existing computer program (e.g., a set of instructions in memory). When a program supports plug-ins, it enables customization of that program. For example, plug-ins can be used in web browsers to add new features such as, but not limited to, search-engines, virus scanners, or the ability to interpret a new file type.

Figure 3:
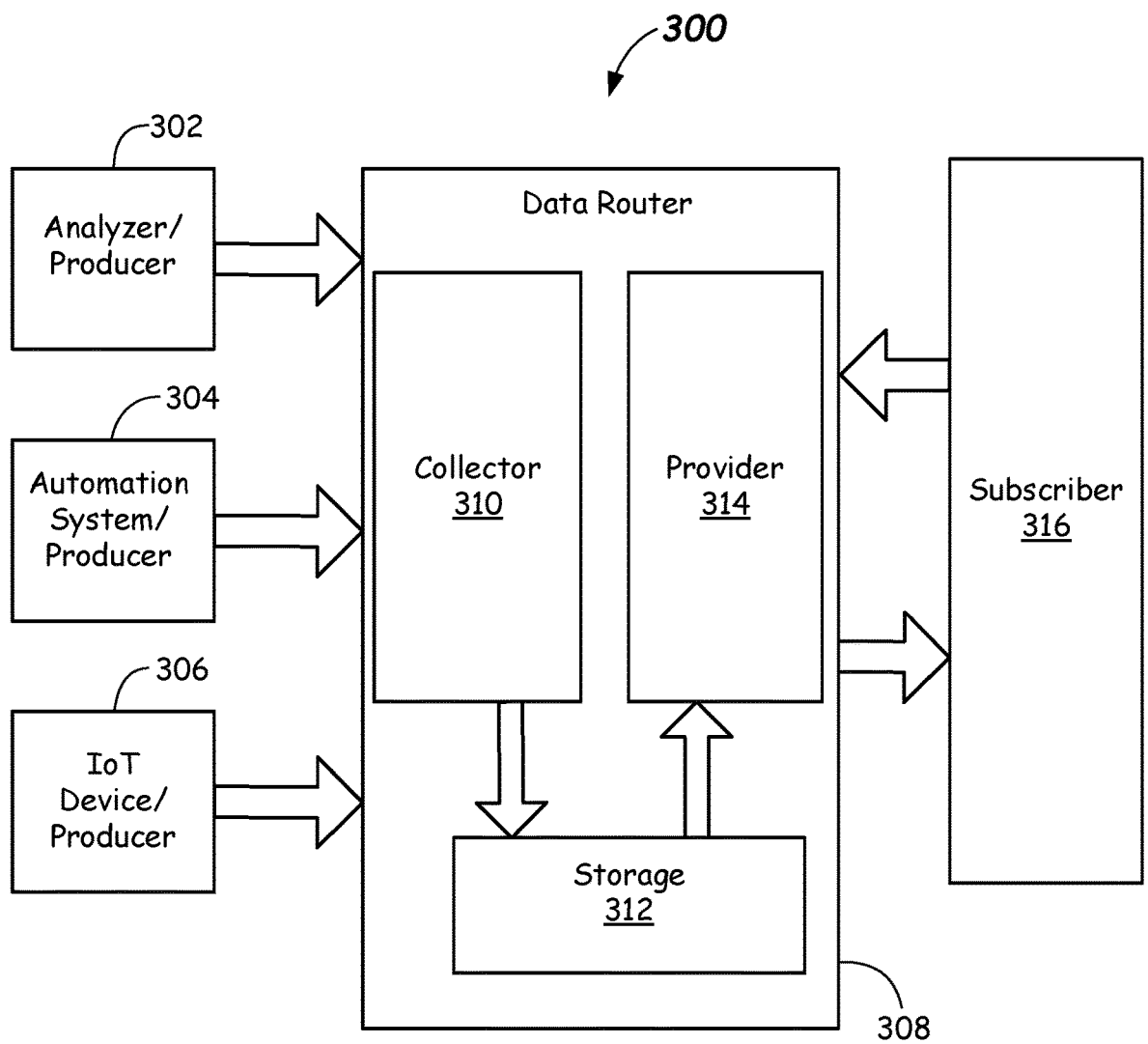
FIG. 3 illustrates a block diagram of producers and a subscriber coupled by a data router, and various internal blocks of a data router in accordance with various alternative example embodiments.

FIG. 3 illustrates an example diagnostic laboratory network 300, in accordance with some embodiments of this disclosure, having producers 302, 304, and 306. In this example embodiment, producers 302, 304, and 306 are each configured to measure various parameters, generate, and/or obtain data or information, and produce, via hardware or hardware/software combinations, packets of data or information in a native format, i.e., a producer-specific format, which are then communicated to a data router 308 via a communications network. Data router 308 is configured to produce records based, at least in part, on the respective packets, with the records being in a common format. In this example embodiment, producer 302 is an analyzer such as, but not limited to, a blood analyzer. Producer 304 is an automation system that provides a track system for moving samples between, for example, analyzers. Producer 306 is an IoT device, including one or more sensors such as, but not limited to, temperature sensors, pressure sensors, infrared sensors, light sensors, ultraviolet sensors, X-ray sensors, voltage sensors, current sensors, magnetic sensors, acceleration sensors, barometers, humidity sensors, and water ionization sensors. Producers 302, 304, and 306, communicate information that they respectively obtain in the course of their operations. In this example embodiment, the information from the producers is in a native format, i.e., a producer-specific format.

In the example embodiment of FIG. 3, data router 308 may be a computer system, and information may be communicated between producers 302, 304, 306 respectively, and data router 308 via any suitable communications network, wired or wireless. In some example embodiments, the communications network is an Ethernet network. Data router 308 may be organized functionally into a collector module 310, a storage module 312, and a provider module 314. In various example embodiments, collector module 310 is responsible for managing the low-level communication protocols used to communicate with the producers and to translate the data received from the producers into records having, among other things, key-value pairs. Collector module 310 stores the records it generates in storage module 312. Provider module 314 is responsible for retrieving records from storage module 312 and delivering those records to one or more subscribers in accordance with previously established subscriptions. Subscriptions are pre-arranged requests by subscribers to receive records from data router 308, based on channels and topics. Subscriptions are set up by communication between the subscribers and data router 308. In some embodiments, the records associated with a requested channel and topic, or the special "all" topic that requests all topics for the specified channel, are delivered to the subscriber as those records become available. In some embodiments, the records are stored by data router 308 until the requesting subscriber is available to receive the requested records.

Still referring to FIG. 3, a subscriber 316 is shown communicatively coupled to data router 308 wherein subscriber 316 is a process manager. Subscriber 316 may be implemented as a computer system executing one or more programs. As described above, a subscriber may make a request to receive data or information, originally generated by a producer (e.g., one or more of producers 302, 304, and 306), from data router 308. In such an arrangement, subscriber 316 receives data or information as records including key-value pairs generated by data router 308 based on data received from one or more of producers 302, 304, and 306. This technological solution provides subscribers with an improved ability to integrate additional producers into a diagnostic laboratory system without having to make changes to the subscriber. Because subscribers receive data or information from data router 308 in a producer-independent, common format, that is organized to provide information to the subscribers in a predetermined format regardless of the source of the data or information, the subscribers' processing burden is reduced compared to first having to determine which producer-specific format is being used, and then choosing specific software modules to execute in order to extract useable information. By reducing the subscribers' processing burden in accordance with embodiments of this disclosure, the subscribers' ability to quickly respond to information is improved.

Additionally, in various embodiments, the data router 308 may serve as a protocol fan-out point. Since many producer-specific protocols are point-to-point only, without data router 308 serving as a protocol fan-out point only one subscriber, rather than any subscriber, could receive information from that producer having a point-to-point protocol. Because data router 308 may be an endpoint for the producer's point-to-point protocol, data router 308 may fan-out the information to any subscriber registered with data router 308. In this way, new subscribers can be added to a diagnostic laboratory system and have the ability to receive information from a producer that otherwise would be limited to delivering its information to a single designated receiver via a point-to-point only connection.

Figure 4A:
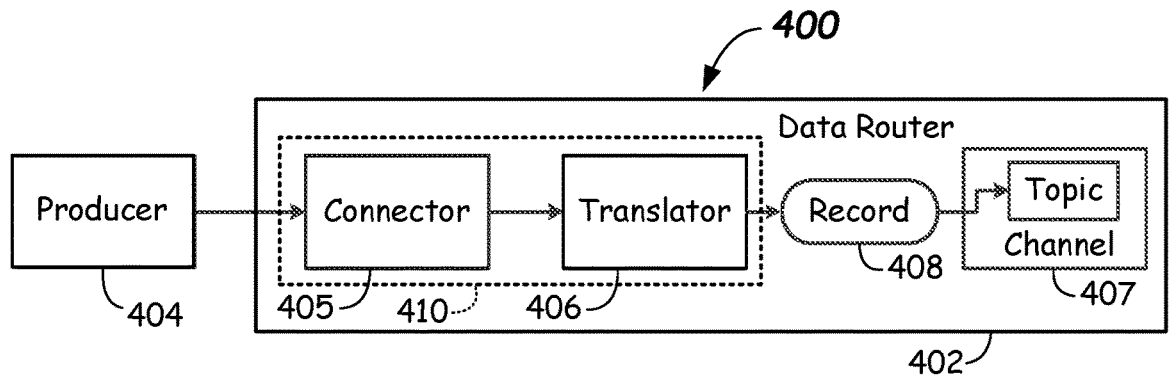
FIG. 4A illustrates a block diagram of a protocol processing model of data router operation in accordance with various example embodiments.

FIG. 4A illustrates an example protocol processing model 400. A data router 402 provides a mechanism for facilitating the integration of diagnostic laboratory devices, such as producer 404. In various embodiments, data router 402 may provide access to a variety of laboratory data sources including, but not limited to, analyzers, instruments, automation, and informatics devices, in a semi-structured data model for purposes such as but not limited to real-time monitoring, business intelligence, and data analytics. Various embodiments of data router 402 may provide access to data from originating laboratory data producers, and publish that data to any interested data consumer, or subscriber, using, for example, standard Hypertext Transfer Protocol (HTTP).

In some embodiments in accordance with this disclosure, data router 402 uses a list of connectors, such as connector 405 in FIG. 4A. As used herein, "connector" refers to one or more software modules that may be stored in a memory of data router 402, and are executable by data router 402. Connector 405 represents a logical connection to a data producer 404. Connector 405 is responsible for any low-level protocol required to communicate with producer 404. While only a single connector is shown in FIG. 4A, it will be understood that data router 402 may have many connectors, such as one or more connectors for each producer. Data router 402 further includes one or more translators 406. Translators 406 may be implemented as one or more software modules that may be stored in a memory of, and executed by, data router 402. Translators 406 may be used to turn raw messages into structured records. In some embodiments, a special "raw" translator may be used to pass along the original message, rather than as reformatted structured records.

Data router 402 also uses a list of channels 407 which represent a sequence of records 408 in a particular format from one or more connectors. Connectors process the data received from the connected device, i.e., producer 404 and produce messages which may be further processed by data router 402. The format of the records 408 assigned to a particular channel is defined by the channel's translator. Records 408 produced by a translator are assigned to a topic. A topic represents a record subtype within its associated channel and is used to filter unwanted records from the channel. The set of connectors 405 and translators 406 is collectively referred to as a collector 410.

Figure 4B:
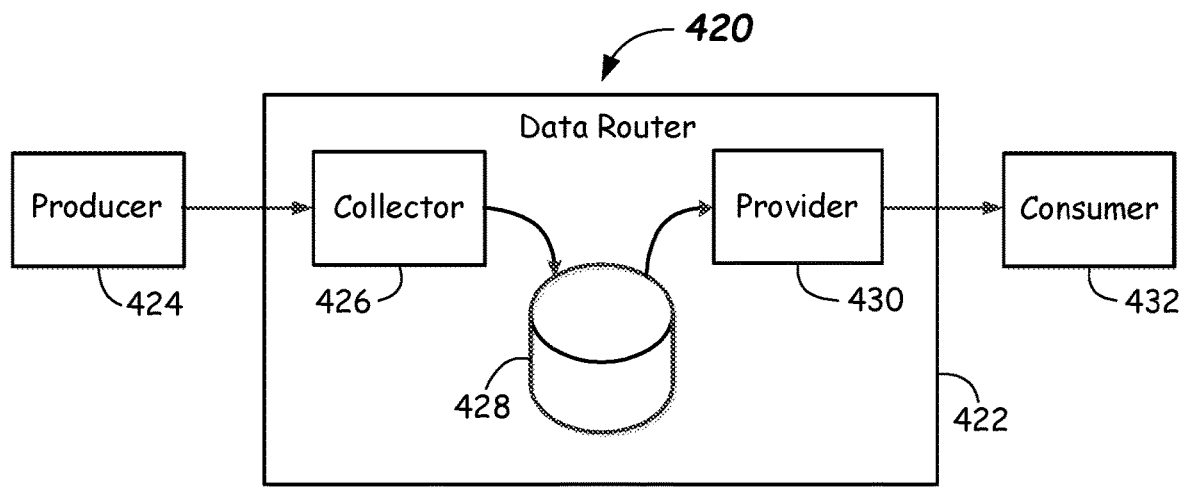
FIG. 4B illustrates a block diagram of a streaming model of data router operation in accordance with various example embodiments.

Referring to FIG. 4B, data model 420 of a diagnostic laboratory is shown that includes a data router 422, a data producer 424, a collector 426, a storage device 428, a provider 430, and a data consumer, or subscriber 432. In some embodiments, subscriber 432, may subscribe to a channel and to a topic to notify data router 422 that subscriber 432 is interested in receiving records associated with that channel and topic. In some embodiments, subscriber 432 may subscribe to a special "all" topic for a particular channel to notify data router 422 that subscriber 432 is interested in receiving all topics for the specified channel. In this example embodiment, each topic is associated with a single channel, and each channel has an associated set of topics. After establishing a connection between subscriber 432 and data router 422, subscriber 432 creates a subscription that tells data router 422 to store the records associated with that subscription until subscriber 432 successfully receives those records. In some embodiments, data router 422 then provides a subscriber ID to subscriber 432. When subscriber 432 reestablishes a connection, data router 422 uses the subscription ID to identify any subscriptions previously created by subscriber 432.

Still referring to FIG. 4B, in some example embodiments, subscriber 432 subscribes to a streaming channel and topic, and receives data from that channel and topic, through one of two HTTP interfaces. For example, a pull interface uses HTTP GET, and may allow subscriber 432 to pull new data from data router 422. A push interface may use WebSockets, and data router 422 may push new data to subscriber 432. A push interface minimizes latency, and is therefore more suitable for near real-time applications. The push and pull interfaces are collectively referred to as the provider 430.

In some example embodiments, data router 422 includes a failure recovery mechanism to ensure all streaming data is delivered to subscriber 432. In the streaming model, data router 422 keeps track of the sequence of records that have been received from a producer, and that have been successfully transferred to a subscriber. Data router 422 stores these records in, for example, a database, until all subscriptions have been satisfied. Streaming records may be numbered in sequence, for example. Subscriber 432 may acknowledge the last record sequence number that was received indicating to data router 422 that it may remove from storage the corresponding record and any previous records associated with the subscription. Internally, data router 422 tracks the next record sequence number to send to the subscriber. Upon failure of either data router 422 or subscriber 432 the next record sequence number can be set to the last successfully received record plus one. The next record sequence number in combination with the last acknowledged sequence number allows the consumer to pick up where it left off and ensures that no record is lost.

Additionally, each topic may have an associated retention policy that defines how records for that topic are retained. For example, in one retention policy, records may be retained until all subscriptions for the record are satisfied, or until the record expires (e.g., after a predetermined time or event). In another example retention policy, the last N records are retained (where N is an integer). In a further example retention policy, records are retained until a specified period of time has elapsed, or until a specific date and time is reached. In some example embodiments, data router 422 includes a special metadata channel that provides information about data router 422 itself. Such information may include, but is not limited to, connector status, up time, throughput rates, subscription status, network errors, memory errors, component failures, overvoltage detection, overheating detection, overclocking detection, power failure detection, and the like.

Figure 4C:
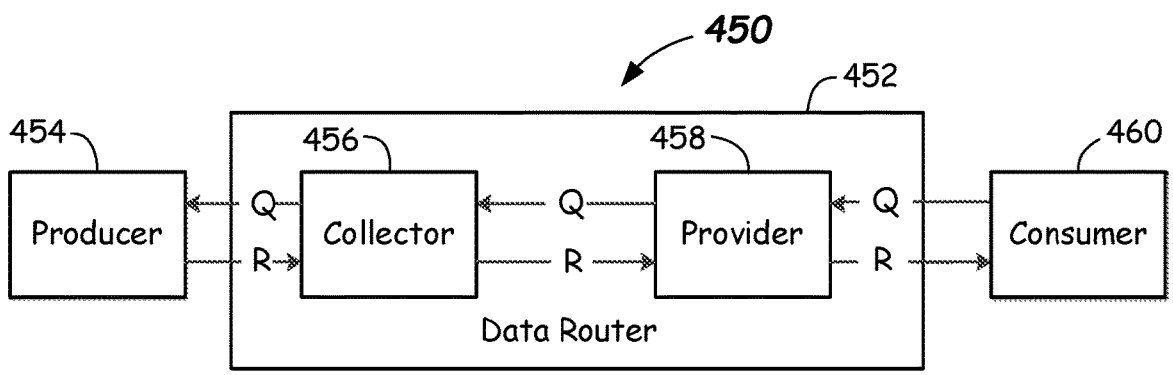
FIG. 4C illustrates a block diagram of a query model of data router operation in accordance with various example embodiments.

Referring to FIG. 4C, a query/response data model 450 of an example diagnostic laboratory system in accordance with this disclosure is shown. In this embodiment, a data router 452 is communicatively coupled to a producer 454. Data router 452 includes collector module 456 and provider module 458, which are communicatively coupled to each other. A subscriber 460 is communicatively coupled to data router 452. In this arrangement, data router 452 does not store translated records. Rather, no records are retained by data router 452, and instead a request for a particular record by subscriber 460 is forwarded by data router 452 to producer 454. Producer 454 then provides the requested information to data router 452, which translates the information into the common format that includes, but is not limited to, key-value pairs. The translated records are then provided by data router 452 to subscriber 460.

Figure 5:
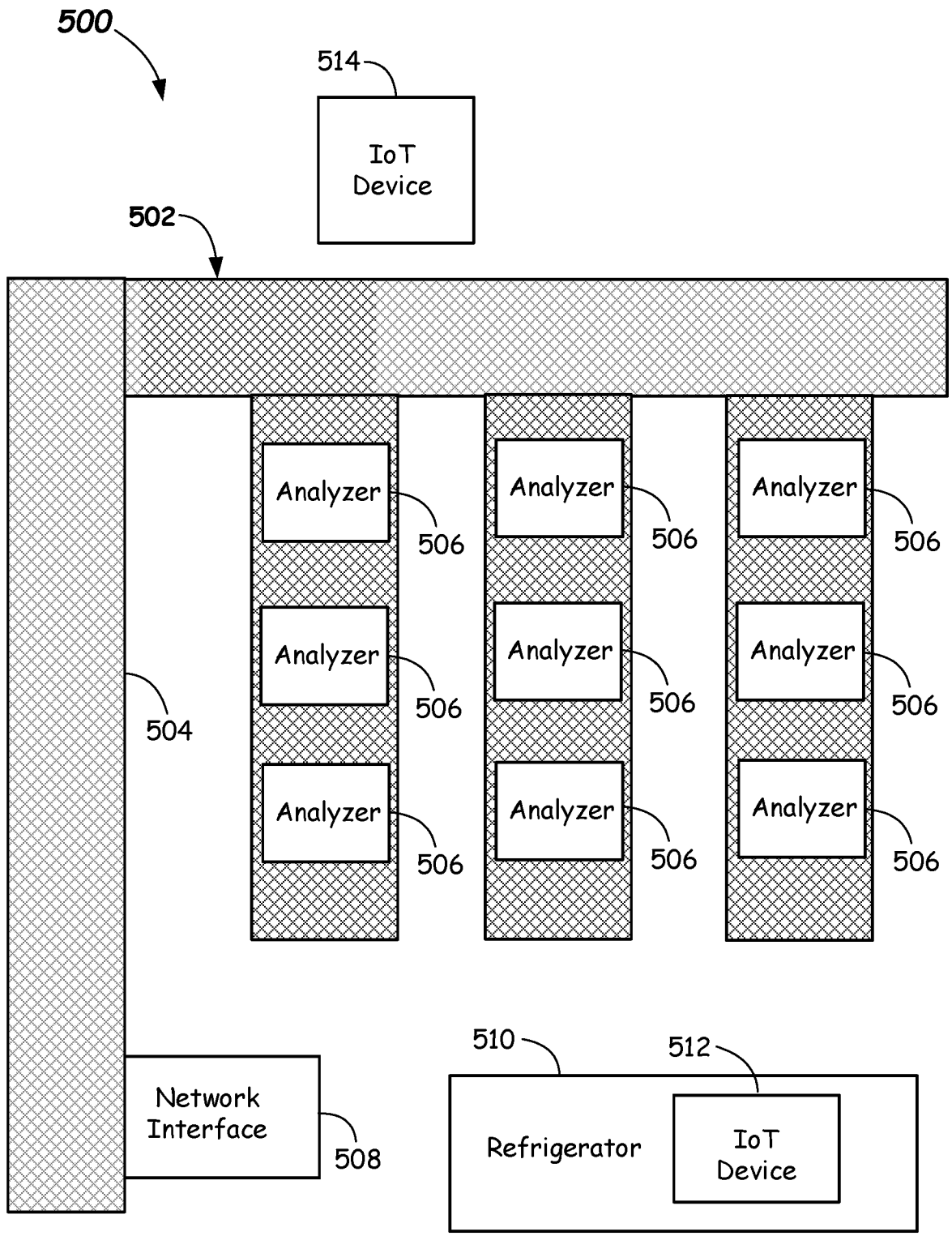
FIG. 5 illustrates an example diagnostic laboratory in accordance with various example embodiments.

FIG. 5 provides a high-level block diagram of a diagnostic laboratory system 500 in accordance with various embodiments of this disclosure. The diagnostic laboratory system of FIG. 5, includes an automation system 502 having a track system 504 suitable for the transport of samples or specimens, in containers, to and from a plurality of various analyzers 506. Automation system 502 may also include a network interface 508 by means of which communications between automation system 502 and a data router (not shown in FIG. 5), such as data router 108, 208, 308, 402, 422 or 452 may be conducted. Automation system 502 may be configured to communicate the data or information from various lab stations, such as but not limited to, analyzers and centrifuges, to a data router via network interface 508. Network interface 508 may be any suitable hardware, or hardware/software combination, for conducting communications with a data router. Such communications may be wired, wireless, or a combination of wired and wireless.

Still referring to FIG. 5, a diagnostic laboratory system may include a refrigerator 510, having an associated IoT device 512. Refrigerator 510 may be used to store samples or specimens at an appropriate temperature. IoT device 512 may sense or measure the temperature of the interior of refrigerator 510 and communicate the results of such sensing or measurement, by wired or wireless communication networks, to a data router. Similarly, an IoT device 514 may sense or measure one or more environmental attributes such as, but not limited to, temperature and humidity, and communicate the results of such sensing or measurement, by wired or wireless communication networks, to a data router.

It is noted that automation system 502 may also include other apparatus such as but not limited to centrifuges (not shown) disposed cooperatively with the track system 504 to deliver and pickup sample or specimen containers. Diagnostic laboratory systems including track systems are well known in, for example, medical diagnostic laboratory settings, for example, the Aptio® Laboratory Automation System, available from Siemens Healthcare Diagnostics, Inc. In operation, tracks convey sample or specimen containers between various lab stations such as, but not limited to, analyzers and centrifuges. Robots may be used to transfer sample or specimen containers from the track to a lab station (e.g., analyzer, centrifuge, etc.) and from a lab station to the track. The aforementioned lab stations, may collect and/or generate data or information in the course of their respective operations, and communicate that data or information to automation system 502.

Still referring to FIG. 5, in some embodiments, one or more analyzers 506 may communicate with a data router (not shown in FIG. 5) with or without also communicating their data to automation system 502.

Figure 6:
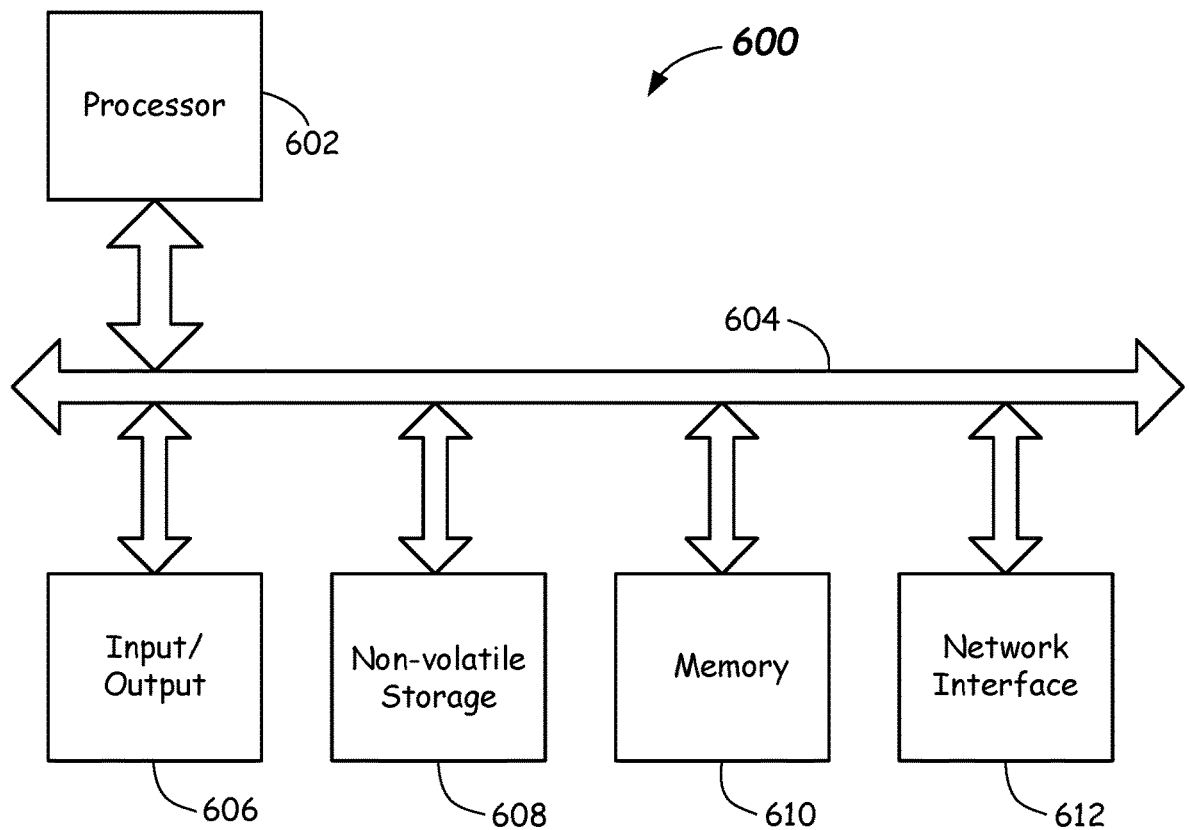
FIG. 6 illustrates an example computer system in accordance with various example embodiments.

FIG. 6 shows a high-level block diagram of an example computer system 600. In this example embodiment, a processor 602 may be coupled to other components of computer system 600 by a bus 604. An input/output device 606, such as but not limited to a display or a keyboard may be coupled to bus 604. A non-volatile storage 608, such as but not limited to a hard disk drive or a flash memory, may be coupled to bus 604. A memory 610, such as but not limited to a dynamic random access memory (DRAM), may be coupled to bus 604. Memory 610 may be configured to store therein instructions that may be executed by processor 602, and may be further configured to store data that does not represent instructions to be executed by processor 602, such as but not limited to, tables that include data or information in a predetermined logical arrangement. A network communications interface 612, such as but not limited to an Ethernet interface, may be coupled to bus 604. Network communications interface 612 provides a communications connection for computer system 600 to a communications network such as, but not limited to, a local area network, or via routers, to the Internet. In one or more embodiments, analyzer 102, 202, or 302, and data router 108, 208, 308, 402, 422 or 452 may include a computer system such as or similar to computer system 600. Analyzers, automation systems, and the like, and/or data routers that include a computer system similar to computer system 600, further include programs, i.e., instructions, stored in a storage device and/or in a memory such as but not limited to non-volatile storage 608 and memory 610, respectively. In operation, such analyzers, automation systems, and the like, and/or data routers that include a computer system similar to computer system 600, may execute instructions stored in their respective memories 610 by their respective processors 602 to implement functions such as, but not limited to, controlling the operations of sensors, managing hardware and software resources, managing communication, and managing memory and storage utilization.

Figure 7:
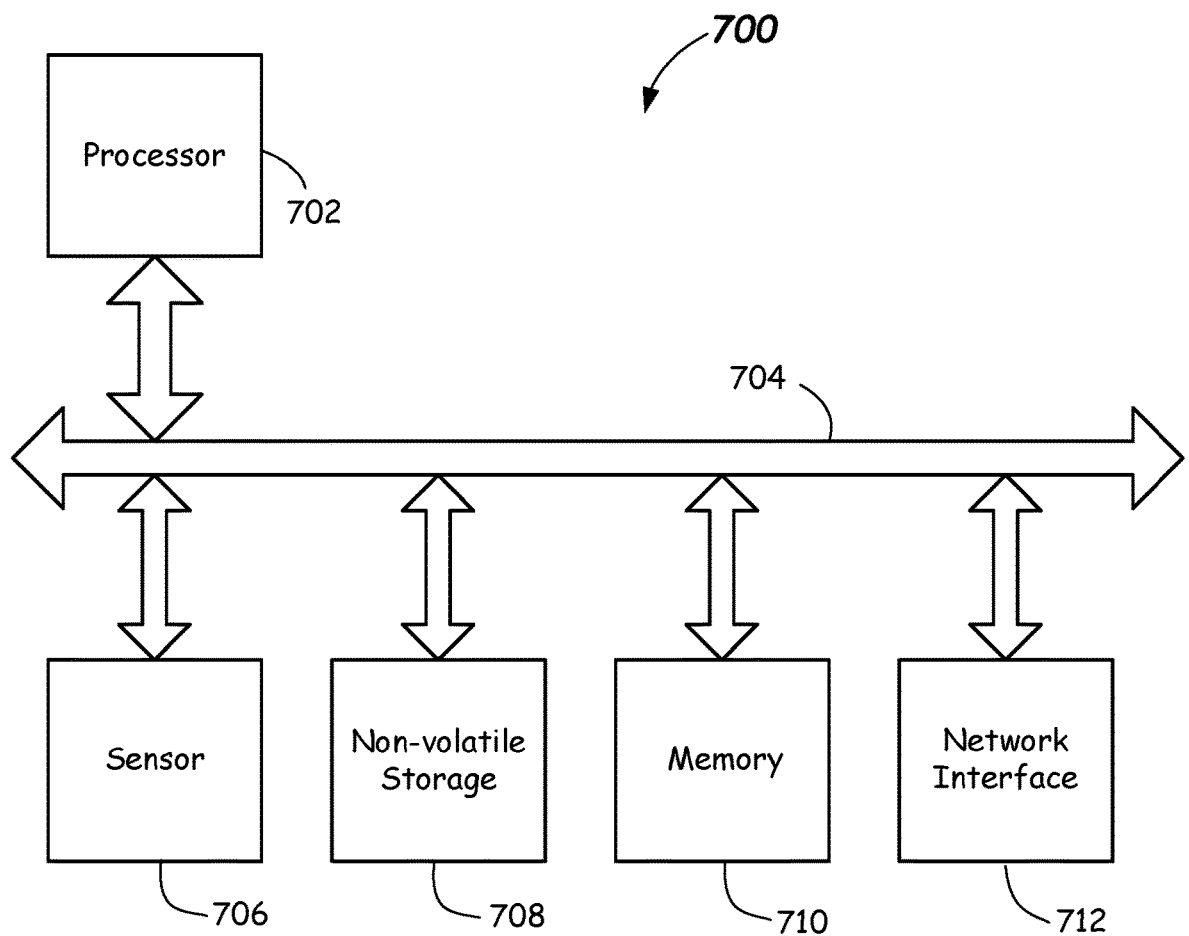
FIG. 7 illustrates an example Internet of Things (IoT) device in accordance with various example embodiments.

FIG. 7 shows a high-level block diagram of an example IoT device 700. In this example embodiment, a processor 702 may be coupled to other components of IoT device 700 by a bus 704. A sensor 706, such as, but not limited to a temperature sensor, may be coupled to bus 704. A non-volatile storage 708, such as but not limited to a hard disk drive or a flash memory, may be coupled to bus 704. A memory 710, such as but not limited to a dynamic random access memory (DRAM), may be coupled to bus 704. Memory 710 may be configured to store therein instructions that may be executed by processor 702, and may be further configured to store data that does not represent instructions to be executed by processor 702. A network communications interface 712, such as but not limited to an Ethernet interface, may be coupled to bus 704. Network interface 712 provides a communications connection for IoT device 700 to a communications network such as, but not limited to, a local area network, or via routers, to the Internet. In one or more embodiments, IoT device 106, 206, or 306 may be similar to IoT device 700. In operation, such IoT devices similar to IoT device 700, may execute instructions stored in their respective memories 710 by their respective processors 702 to implement functions such as, but not limited to, operating their respective sensors, and generating a packet of data or information in a predetermined format.

In one example embodiment, a producer such as an IoT device including sensors configured to measure temperature and humidity in a diagnostic laboratory, operates its sensors to make one or measurements, and sends its sensor-generated data, in a producer specific format, to a data router. The data router may translate the sensor-generated, and any other data, that it receives from the producer into a common format to be used in communicating with one or more subscribers. The data router's translation process includes generating records that are stored in the data router. Each record may be assigned an identifier. In some embodiments, the identifier may be, for example, a 64-bit integer identifier (ID). In this example process, the ID may start at 1 when the data router first begins, and is monotonically increased. The data router may send one or more records to the subscriber in a single "batch," and may also provide the ID of the last record only. In this example embodiment, the subscriber is supposed to process the received data and then acknowledge the last record, by send back to the data router the ID that was provided to it by the data router. The purpose of this mechanism is failure recovery, and supports "at least once" semantics.

Figure 8A:
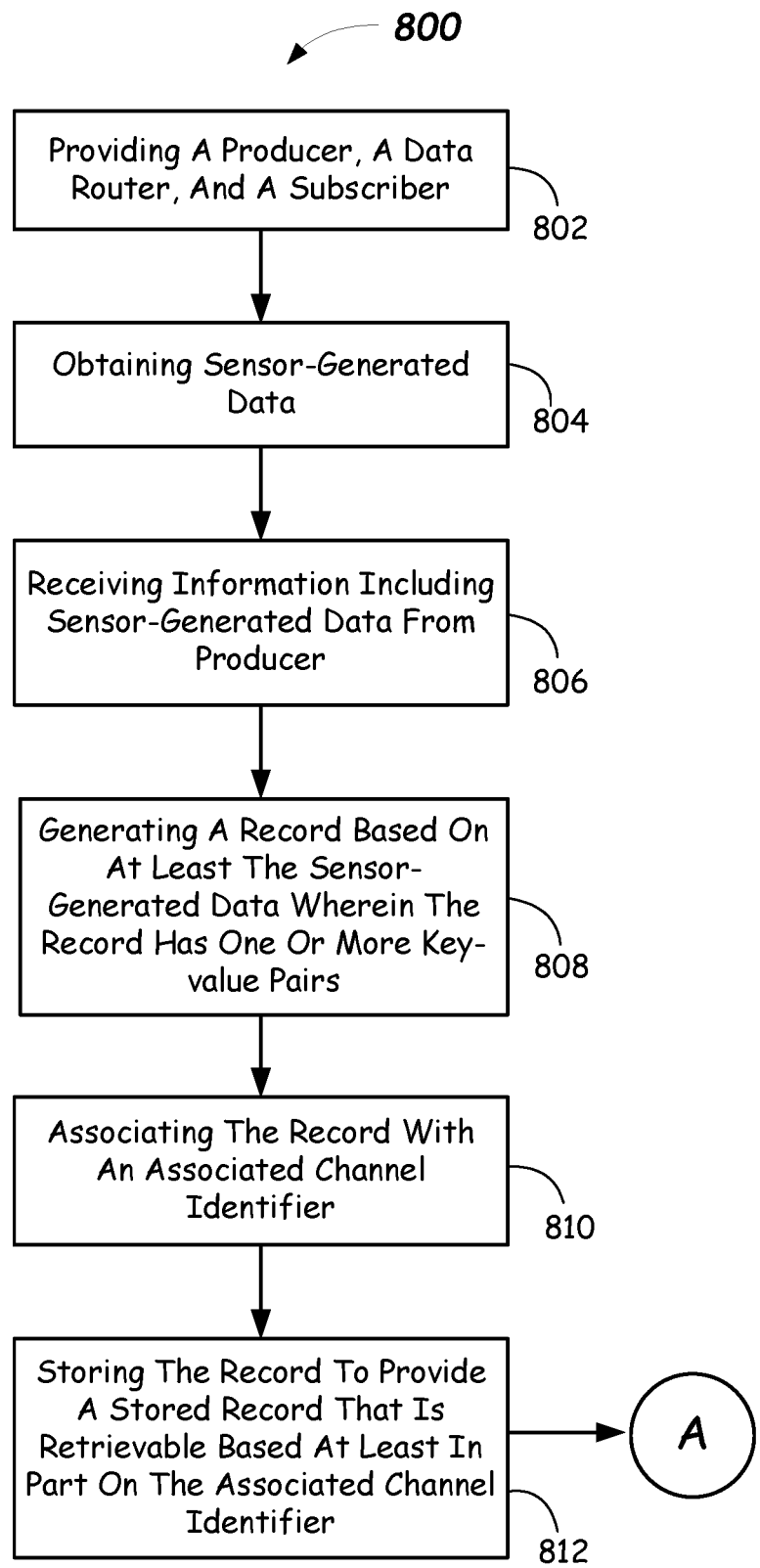
FIGS. 8A-8B illustrate an example method of operating a diagnostic laboratory in accordance with various example embodiments.
Figure 8B:
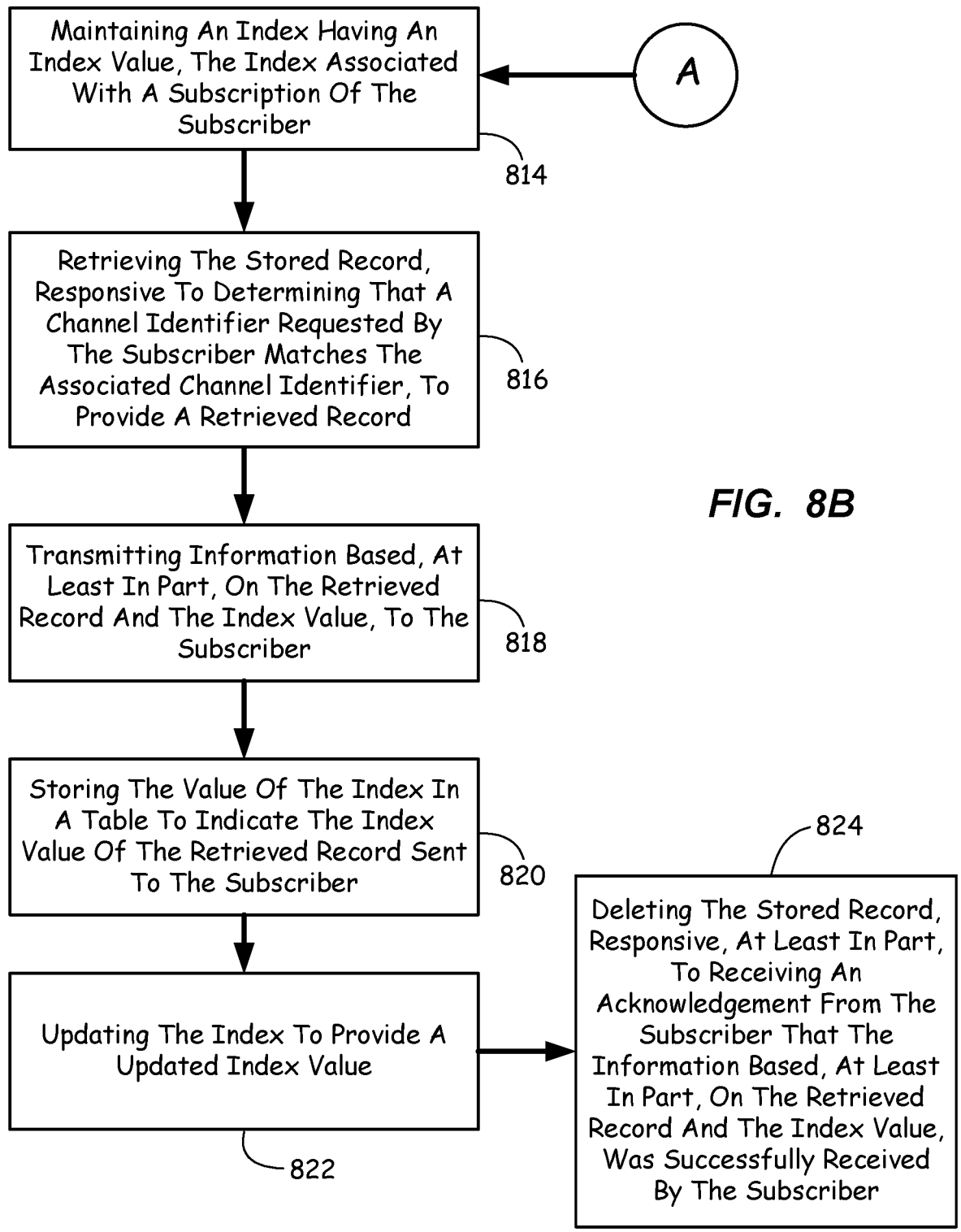

FIGS. 8A-8B illustrate a flow diagram of an example method 800 of operating a diagnostic laboratory system to provide sensor-generated information. With reference to method 800, in Block 802, a producer, a data router, and a subscriber are provided. Together, one or more producers, a data router, and one or more subscribers may form a diagnostic laboratory system. In Block 804, sensor-generated data is obtained by the producer. A producer may operate its one or more sensors to sense or measure a predetermined parameter and obtain the data or information resulting from the sensing or measuring. The sensor-generated data may be obtained via the operation of a device such as, but not limited to, an analyzer, an automation system, or an IoT device. For example, a blood, immunoassay, or clinical chemistry analyzer, after performing one or more testing and/or analysis operations, may obtain the result of those testing and/or analysis operations. Similarly an IoT device may obtain through the operation of its sensors and associated hardware and/or software, readings on temperature, humidity, vibration, weight, barometric pressure, hardware malfunctions, or water ionization, to provide some examples. Method 800 further includes, in Block 806, the data router receiving information including the sensor-generated data from a producer. Communication between the producer and data router may be wired or wireless. In some example embodiments, the communication between the producer and data router takes place without the use of the Internet. By keeping communications local, i.e., without going outside the network of a diagnostic laboratory operator, a greater level of security is provided for the data being communicated. In Block 808, the data router generates a record based on at least the sensor-generated data received from the producer. The data router translates the information received from the producer to produce a record having one or more key-value pairs. In a Block 810, the data router associates the generated record with a channel identifier, referred to as an associated channel identifier. In a Block 812, the record is stored in the data router to provide a stored record that is retrievable based at least in part on the associated channel identifier. For example the record may be stored in a non-volatile storage device, such as but not limited to, a hard disk, or a solid state drive (i.e., flash memory-based storage device) within the data router (see FIG. 3). In some embodiments, the record may have a plurality of fields, such as but not limited to a channel identifier and a topic identifier in addition to one or more key-value pairs. In some embodiments, a processor of the data router may execute software that causes the processor to search the stored records and retrieve one or more of the stored records from the non-volatile storage device based on, for example, the channel identifier field of the records. In a Block 814, the data router maintains an index in the memory of the data router. The index may be one or more addressable locations within the memory. A value, referred to as an index value is stored in the index. The index, i.e., the one or more memory locations that store an index value, are associated with a subscription of the subscriber. In some embodiments, the index value may be used to uniquely specify each record associated with a given channel—for example Record 53 of Channel N, where N is a channel identifier. It will be understood that there may be many records associated with a particular channel, therefore an index value that uniquely identifies one record among a plurality of records associated with that particular channel may be used to select the desired one out of the plurality of records. In a block 816, the data router retrieves a stored record responsive to determining that a channel identifier requested by the subscriber matches the associated channel identifier to provide a retrieved record. In a Block 818, the data router transmits information based, at least in part, on the retrieved record and the index value, to the subscriber. In a Block 820, the data router stores the index value in a table to indicate the index value of the retrieved record sent to the subscriber (see FIG. 9, Last Record Sent ID 908). In a Block 822, the data router updates the index to provide an updated index value. In some embodiments, the updated index value may be used to store the next record that is generated. In some embodiments, the index value may be used by hardware and/or software of the data router to generate an address at which the record is to be stored. In a Block 824, the data router deletes the stored record responsive, at least in part, to receiving an acknowledgement from the subscriber that the information based, at least in part, on the retrieved record and the index value, was successfully received by the subscriber. In various embodiments, the data router and the subscriber engage in a handshaking protocol in which successfully received record data is acknowledged by the subscriber via a return message to the data router identifying the record that was successfully received.

Referring to FIG. 9, an expanded partial view of table 220 of FIG. 2 is shown. This expanded partial view shows an example data structure and the type of information stored by the data router in carrying out its functions. For example, a Subscriber ID 902, Channel ID 904, a Topic ID 906, a Last Record Sent ID 908, and a Last Record Received ID 910, are shown in FIG. 9. In this way, the status of record transmission and successful record reception for a particular subscriber's requested channel and topic can be maintained.

In some alternative embodiments in accordance with this disclosure, a data router and a process manager may be implemented on the same computer system.

In some alternative embodiments in accordance with this disclosure, a first communications network between a publisher and a data router is a different communications network than the one between the data router and a subscriber.

In some alternative embodiments in accordance with this disclosure, a data router and a subscriber may be implemented on the same or different computer systems.

In various example embodiments, a "data packet" is not limited to any particular size, and may include some or all of the data or information that a producer or a data router intends to send as part of any message.

Numerous embodiments are described in this disclosure, and are presented for illustrative purposes only. The described embodiments are not, and are not intended to be, limiting in any sense.

The present disclosure is neither a literal description of all embodiments nor a listing of features that must be present in all embodiments.

When an ordinal number (such as "first," "second," "third," and so on) is used as an adjective before a term, that ordinal number is used (unless expressly specified otherwise) merely to indicate a particular feature, such as to distinguish that particular feature from another feature that is described by the same term or by a similar term. For example, a "first widget" may be so named merely to distinguish it from, e.g., a "second widget." Thus, the mere usage of the ordinal numbers "first" and "second" before the term "widget" does not indicate any other relationship between the two widgets, and likewise does not indicate any other characteristics of either or both widgets. For example, the mere usage of the ordinal numbers "first" and "second" before the term "widget" (1) does not indicate that either widget comes before or after any other in order or location; (2) does not indicate that either widget occurs or acts before or after any other in time; and (3) does not indicate that either widget ranks above or below any other, as in importance or quality. In addition, the mere usage of ordinal numbers does not define a numerical limit to the features identified with the ordinal numbers. For example, the mere usage of the ordinal numbers "first" and "second" before the term "widget" does not indicate that there must be no more than two widgets.

Devices that are in communication with each other need not be in continuous communication with each other, unless expressly specified otherwise. On the contrary, such devices need only transmit to each other as necessary or desirable, and may actually refrain from exchanging data most of the time. For example, a machine in communication with another machine via the Internet may not transmit data to the other machine for weeks at a time. In addition, devices that are in communication with each other may communicate directly or indirectly through one or more intermediaries.

A description of an embodiment with several components or features does not imply that all or even any of such components and/or features are required. On the contrary, a variety of optional components are described to illustrate the wide variety of possible embodiments in accordance with this disclosure. Unless otherwise specified explicitly, no component and/or feature is essential or required.

Further, although process steps, algorithms or the like may be described in a sequential order, such processes may be configured to work in different orders. In other words, any sequence or order of steps that may be explicitly described does not necessarily indicate a requirement that the steps be performed in that order. The steps of processes described herein may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to implement various embodiments in accordance with this disclosure, and does not imply that the illustrated process is preferred.

An enumerated list of items (which may or may not be numbered) does not imply that any or all of the items are mutually exclusive, unless expressly specified otherwise. Likewise, an enumerated list of items (which may or may not be numbered) does not imply that any or all of the items are comprehensive of any category, unless expressly specified otherwise. For example, the enumerated list "a computer, a laptop, a PDA," does not imply that any or all of the three items of that list are mutually exclusive and does not imply that any or all of the three items of that list are comprehensive of any category.

A "processor" means any one or more microprocessors, Central Processing Unit (CPU) devices, one or more Central Processing Units (CPUs), one or more Graphics Processing Units (GPUs), one or more computing devices, one or more microcontrollers, one or more digital signal processors, one or more embedded processors such as an embedded processor in a System on Chip (SoC), one or more field programmable gate arrays (FPGAs), like devices, or various combinations of the foregoing.

While it is contemplated that an appropriately programmed general purpose computer or computing device may be used, it is also contemplated that hard-wired circuitry or custom hardware (e.g., one or more application specific integrated circuits (ASICs), or one or more configured field programmable gate arrays (FPGAs)) may be used in place of, or in combination with, software instructions for implementation of the processes of various embodiments. Thus, embodiments are not limited to any specific combination of hardware and software.

The term "computer-readable medium" refers to any statutory medium that participates in providing data (e.g., instructions) that may be read by a computer, a processor or a like device. Such a medium may take many forms, including but not limited to non-volatile media, volatile media, and specific types of transmission media. Non-volatile media include, for example, optical disks, magnetic disks, and other persistent memory. Volatile media include, but are not limited to, static random access memory (SRAM), and dynamic random access memory (DRAM). Types of transmission media include, for example, coaxial cables, electrically conductive wires, traces, or lines, including the wires, traces, or lines that comprise a system bus coupled to the processor, and optical fibers. Common forms of computer-readable media include, for example, a floppy disk, a flexible disk, hard disk, magnetic tape, any other magnetic medium, a CD-ROM, Digital Video Disc (DVD), any other optical medium, punch cards, paper tape, any other physical medium with patterns of holes, a read-only memory (ROM), a random access memory (RAM), a programmable read-only memory (PROM), an electrically programmable read-only memory (EPROM), an electrically erasable programmable read-only memory (EEPROM), a flash memory (a type of EEPROM), a resistive memory, a filamentary memory, a metal oxide memory, a phase change memory, a spin transfer memory, a USB memory stick, any other memory chip or cartridge, or any other medium from which a computer, or processor, can access the data or instructions stored therein. The terms "computer-readable memory" and/or "tangible media" specifically exclude signals, waves, and wave forms or other intangible or non-transitory media that may nevertheless be readable by a computer.

An enumerated list of items (which may or may not be numbered) does not imply that any or all of the items are mutually exclusive, unless expressly specified otherwise. Likewise, an enumerated list of items (which may or may not be numbered) does not imply that any or all of the items are comprehensive of any category, unless expressly specified otherwise. For example, the enumerated list "a computer, a laptop, a smartphone" does not imply that any or all of the three items of that list are mutually exclusive and does not imply that any or all of the three items of that list are comprehensive of any category.

The foregoing description discloses only example embodiments. Modifications of the above-disclosed apparatus and methods which fall within the scope of this disclosure will be readily apparent to those of ordinary skill in the art. For example, although the examples discussed above are illustrated for health information systems, other embodiments in accordance with this disclosure can be implemented for other markets.

What is claimed is:

1. A method of operating a diagnostic laboratory system to provide sensor-generated information, comprising:
   providing a producer, a data router, and a subscriber;
   obtaining, by the producer, sensor-generated data;
   receiving, by the data router, information, including sensor-generated data, from the producer;
   generating, by the data router, a record based on at least the sensor-generated data from the producer, wherein the record has one or more key-value pairs;
   associating, by the data router, the record with an associated channel identifier;

storing, by the data router, the record to provide a stored record such that the stored record is retrievable based, at least in part, on the associated channel identifier;

maintaining, by the data router, an index having an index value, the index associated with a subscription of the subscriber;

retrieving, by the data router, the stored record, responsive to determining that a channel identifier requested by the subscriber matches the associated channel identifier to provide a retrieved record;

transmitting, by the data router, information based, at least in part, on the retrieved record and the index value, to the subscriber;

storing the index value, by the data router, in a table to indicate the index value of the retrieved record sent to the subscriber;

updating the index, by the data router, to provide a updated index value; and deleting, by the data router, the stored record, responsive, at least in part, to receiving an acknowledgement from the subscriber that the information based, at least in part, on the retrieved record and the index value, was successfully received by the subscriber;

wherein the producer includes at least one sensor, and a first computational resource, the first computational resource comprising a processor, at least one communications network interface, and a memory having stored therein a plurality of instructions, wherein the data router includes at least one communications network interface, and a second computational resource comprising a processor, and a memory having stored therein a plurality of instructions and a plurality of tables, wherein the producer includes a third computational resource comprising a processor, at least one communications network interface, and a memory having stored therein a plurality of instructions, wherein the sensor-generated data from the producer is obtained, at least in part, from operation of at least one sensor coupled to the producer, the at least one sensor disposed external to the data router.

2. The method of claim 1, further comprising:
associating, by the data router, the record with an associated topic identifier.

3. The method of claim 1, further comprising transmitting information from the producer to the data router via an Ethernet local area network.

4. The method of claim 1, further comprising transmitting information from the data router to the subscriber via an Ethernet local area network.

5. The method of claim 1, further comprising deleting, by the data router, the stored record, responsive, at least in part, to an expiration of the record.

6. The method of claim 1, further comprising deleting, by the data router, the stored record, responsive, at least in part, to a predetermined number of newer stored records being stored.

7. The method of claim 1, further comprising deleting, by the data router, the stored record, responsive, at least in part, to the detection of a specific date and time.

8. The method of claim 1, further comprising deleting, by the data router, the stored record, responsive, at least in part, to the stored record having been retained for a predetermined period of time.

9. The method of claim 1, further comprising:
adding a second producer to the diagnostic laboratory system; and installing a plug-in in the data router to translate information received by the data router from the second producer.

10. The method of claim 1, further comprising associating, by the data router, the record with an associated topic identifier.

11. A data router, comprising:
at least one communications network interface; and
a computational resource comprising a processor, and a memory having stored therein at least one table, at least one index, and a plurality of instructions that, when executed by the processor, cause the data router to:
receive information, including sensor-generated data in a first format, from a producer;
translate the information to generate a record based on at least the sensor-generated data in the first format, wherein the record is in a second format and has one or more key-value pairs;
associate the record with an associated channel identifier;
store the record to provide a stored record such that the stored record is retrievable based, at least in part, on the associated channel identifier;
maintain an index having an index value, the index associated with a subscription of a subscriber;
retrieve the stored record, responsive to determining that a requested channel identifier of the subscription of the subscriber matches the associated channel identifier, to provide a retrieved record;
transmit to the subscriber, information based, at least in part, on the retrieved record and the index value;
store the index value in a first table of the at least one table, to indicate the index value of the retrieved record sent to the subscriber;
update the index to provide an updated index value; and
delete the stored record, responsive, at least in part, to receiving an acknowledgement from the subscriber that the information based, at least in part, on the retrieved record and the index value, was successfully received by the subscriber.

12. The data router of claim 11, wherein the plurality of instructions, when executed by the processor, further cause the data router to delete the stored record responsive to expiration of the stored record.

13. The data router of claim 11, wherein the plurality of instructions, when executed by the processor, further cause the data router to delete the stored record responsive to a predetermined number of newer stored records being stored.

14. The data router of claim 11, wherein the plurality of instructions, when executed by the processor, further cause the data router to delete the stored record responsive to the detection of a specific date and time.

15. The data router of claim 11, wherein the plurality of instructions, when executed by the processor, further cause the data router to delete the stored record responsive to the stored record having been retained for a predetermined period of time.

16. A diagnostic laboratory system, comprising:
a producer;
a subscriber;
a data router communicatively coupled to the producer, and communicatively coupled to the producer, the data router comprising:
at least one communications network interface; and
a first computational resource comprising a processor, and a memory having stored therein a plurality of tables, and having a plurality of instructions stored therein that, when executed by the processor, cause the data router to:
receive information, including sensor-generated data in a first format, from the producer;
generate a record based on at least the sensor-generated data in the first format from the producer, wherein the record is in a second format and has one or more key-value pairs;
associate the record with an associated channel identifier;
store the record to provide a stored record such that the stored record is retrievable based, at least in part, on the associated channel identifier;
maintain an index having an index value, the index associated with a subscription of the subscriber;
retrieve the stored record, responsive to determining that a requested channel identifier of the subscription of the subscriber matches the associated channel identifier, to provide a retrieved record;
transmit to the subscriber, information based, at least in part, on the retrieved record and the index value;
store the index value in a first table of the plurality of tables, to indicate the index value of the retrieved record sent to the subscriber;
update the index to provide an updated index value; and
delete the stored record, responsive, at least in part, to receiving an acknowledgement from the subscriber that the information based, at least in part, on the retrieved record and the index value, was successfully received by the subscriber;
wherein the producer includes at least one sensor, and a second computational resource, the second computational resource comprising:
a processor, at least one communications network interface, and a memory having stored therein a plurality of instructions that, when executed by the processor, cause the producer to:
operate the at least one sensor; and
obtain sensor-generated data,
wherein the subscriber includes a third computational resource comprising:
a processor, at least one communications network interface, and a memory having stored therein a plurality of instructions that, when executed by the processor, cause the subscriber to:
register with the data router; and
receive information based, at least in part, on the retrieved record and the index value.

17. The diagnostic laboratory system of claim 16, wherein the second format is a subscriber-readable format.

18. The system of claim 16, further comprising:
obtaining, by the producer, non-sensor-generated status information, wherein the non-sensor-generated status information is indicative of a status of the producer.

19. The diagnostic laboratory system of claim 18, wherein the plurality of instructions stored in the memory of the first computational resource, when executed by the processor of the first computational resource, further cause the data router to:
generate a record based on at least the non-sensor-generated status information from the producer, wherein the record is in a second format and has one or more key-value pairs.

20. The diagnostic laboratory system of claim 16, wherein the first computational resource is configured to include plug-ins.

* * * * *